United States Patent [19]

Berkowitz et al.

[11] Patent Number: 5,045,531

[45] Date of Patent: Sep. 3, 1991

[54] WOUND TREATMENT EMPLOYING BIOLOGICALLY ACTIVE ION CHANNEL FORMING PEPTIDES AND PROTEINS

[75] Inventors: Barry Berkowitz, Ft. Washington; Leonard S. Jacob, Penn Valley, Merion Station, both of Pa.

[73] Assignee: Magainin Sciences Inc., Plymouth Meeting, Pa.

[21] Appl. No.: 451,777

[22] Filed: Dec. 18, 1989

[51] Int. Cl.$^5$ .......................... C07K 7/08; C07C 7/10; A61K 37/02
[52] U.S. Cl. ........................................ 514/12; 514/13; 514/14

[58] Field of Search .............................. 514/12, 13, 14; 530/324, 325, 326

[56] References Cited

U.S. PATENT DOCUMENTS 4,507,230  3/1985  Tam et al. ........................... 530/337

*Primary Examiner*—Lester L. Lee
*Attorney, Agent, or Firm*—Elliot M. Olstein; Raymond J. Lillie

[57] ABSTRACT

A process for treating a wound in a host which comprises administering to the host having a wound at least one biologically active amphiphilic peptide. The peptide is an ion channel-forming peptide and is administered in an amount effective for treating a wound in a host.

33 Claims, No Drawings

WOUND TREATMENT EMPLOYING BIOLOGICALLY ACTIVE ION CHANNEL FORMING PEPTIDES AND PROTEINS

This application relates to wound treatment; in particular, this invention relates to the stimulation of wound healing. More particularly, this invention relates to the stimulation of wound healing by employing a biologically active peptide.

In accordance with an aspect of the present invention, there is provided a process for stimulating healing of a wound in a host, which comprises administering to the host a composition comprising at least one biologically active amphiphilic peptide and/or biologically active protein. The at least one biologically active amphiphilic peptide and/or biologically active protein is administered in an amount effective for stimulating healing of a wound in a host.

The biologically active amphiphilic peptides employed in the present invention are generally water soluble to a concentration of at least 20 mg/ml at neutral pH in water. In addition, the structure of such peptide provides for flexibility of the peptide molecule. When the peptide is placed in water, it does not assume an amphiphilic structure. When the peptide encounters an oily surface or membrane, the peptide chain folds upon itself into a rod-like structure. Such peptides are also preferably non-hemolytic; i.e.; they will not rupture blood cells at effective concentrations.

In general, such peptides have at least 16 amino acids, and preferably at least 20 amino acids. In most cases, such peptides do not have in excess of 50 amino acids.

In general, the biologically active peptides or biologically active proteins employed in the present invention are ion channel-forming peptides or proteins. An ion channel-forming peptide or protein or ionophore is a peptide or protein which increases the permeability for ions across a natural or synthetic lipid membrane. B. Christensen et al. PNAS Vol. 85 P. 5072–76 (July, 1988) describes methodology which indicates whether or not a peptide or protein has ion channel-forming properties and is therefore an ionophore. As used herein an ion channel-forming peptide or protein is a peptide or protein which has ion channel-forming properties as determined by the method of Christensen et al.

An amphiphilic peptide is a peptide which includes both hydrophobic and hydrophilic peptide regions.

The administration of the biologically active amphiphilic peptides or proteins to a host may be by systemic or topical administration in order to stimulate wound healing in a host.

The term "wound healing" as used herein include various aspects of the wound healing process. These aspects include, but are not limited to, increased contraction of the wound, increased deposition of connective tissue, as evidenced by, for example, increased deposition of collagen in the wound, and increased tensile strength of the wound.

Applicants have found that the biologically active peptides or proteins employed in the present invention may be used to stimulate, or promote, wound healing. In particular, applicants have found that the biologically active peptides or proteins may increase contraction of wounds, increase collagen deposition in wounds, and/or increase wound breaking strength. Applicants have found that the biologically active peptides or proteins employed in the present invention reverse the inhibition of wound healing caused by steroids such as cortisone.

In general, the peptide or protein is employed to provide peptide or protein dosages of from 0.1 mg to 250 mg per kilogram of host weight, when administered systemically. When administered topically, the peptide or protein is administered in an amount of from about 0.1% to about 10%, preferably from about 1% to about 2%. The topical composition may be in the form of an ointment, cream, or solution.

The peptides or proteins employed in the present invention, in addition to stimulating or promoting wound healing, are also capable of interacting selectively with membranes of bacteria. Also, the peptides or proteins are effective as an antibiotic, and may inhibit, prevent, or destroy the growth or proliferation of microbes such as bacteria (including Gram-positive and Gram-negative bacteria), fungi, parasites, viruses, or the like. Thus, the peptides or proteins employed in accordance with the present invention may prevent wound contamination and infection while stimulating wound healing. The peptides or proteins may also be administered in combination with antibiotics, or in combination with known wound care products.

In accordance with an embodiment, the peptide employed, or derivatives or analogues thereof, is a basic (positively charged) polypeptide having at least sixteen amino acids wherein the polypeptide includes at least eight hydrophobic amino acids and at least eight hydrophilic amino acids. Still more particularly, the hydrophobic amino acids are in groups of two adjacent amino acids, and each group of two hydrophobic amino acids is spaced from another group of two hydrophobic amino acids by at least one amino acid other than a hydrophobic amino acid (preferably at least two amino acids) and generally by no greater than four amino acids, and the amino acids between pairs of hydrophobic amino acids may or may not be hydrophilic.

The hydrophilic amino acids are generally also in groups of two adjacent amino acids in which at least one of the two amino acids is a basic hydrophilic amino acid, with such groups of two hydrophilic amino acids being spaced from each other by at least one amino acid other than a hydrophilic amino acid (preferably at least two amino acids) and generally no greater than four amino acids, and the amino acids between pairs of hydrophilic amino acids may or may not be hydrophobic.

In accordance with a particularly preferred embodiment, the polypeptide comprises a chain of at least four groups of amino acids, with each group consisting of four amino acids. Two of the four amino acids in each group are hydrophobic amino acids, and two of the four amino acids in each group are hydrophilic, with at least one of the hydrophilic amino acids in each group being a basic hydrophilic amino acid and the other being a basic or neutral hydrophilic amino acid.

The hydrophobic amino acids may be selected from the class consisting of Ala, Cys, Phe, Gly, Ile, Leu, Met, Val, Trp, and Tyr. The neutral hydrophilic amino acids may be selected from the class consisting of Asn, Gln, Ser, and Thr. The basic hydrophilic amino acids may be selected from the class consisting of Lys, Arg, His, and ornithine (O).

Each of the groups of four amino acids may be of the sequence ABCD, BCDA, CDAB, or DABC, wherein A and B are each hydrophobic amino acids and may be the same or different, one of C or D is a basic hydrophilic amino acid, and the other of C or D is a basic or neutral hydrophilic amino acid and may be the same or different. In a preferred embodiment, the polypeptide chain may comprise 5 or 6 groups of this sequence. In each group, each of A, B, C and D may be the same in some or all of the groups or may be different in some or all of the groups.

The polypeptide chain preferably has at least 20 amino acids, and no greater than 50 amino acids. It is to be understood, however, that the polypeptide does not have to consist entirely of the groups described above. The polypeptide may have amino acids extending from either or both ends of the noted groups forming the polypeptide chain and/or there may be amino acids between one or more of the at least four groups and still remain within the scope of the invention.

The groups of amino acids may be repeating groups of amino acids, or the amino acids in the various groups may vary provided that in each group of the at least four groups of amino acids there are two hydrophobic and two hydrophilic amino acids as hereinabove noted.

Thus, in a preferred embodiment, the biologically active polypeptide comprises a chain including at least four groups of amino acids, each containing four amino acids. Two of the four amino acids in each group are hydrophobic, at least one amino acid is basic hydrophilic, and the remaining one is basic or neutral hydrophilic, with the polypeptide chain preferably having at least 20 amino acids but no greater than 50 amino acids.

In one embodiment, each of the at least four groups of amino acids which are in the peptide chain is of the sequence A-B-C-D, B-C-D-A, C-D-A-B or D-A-B-C wherein A and B are hydrophobic amino acids, one of C or D is basic hydrophilic amino acid, and the other of C or D is basic or neutral hydrophilic amino acid. The resulting polypeptide chain, therefore, may have one of the following sequences:

$(X_1)_a(A\text{-}B\text{-}C\text{-}D)_n(Y_1)_b$ $(X_2)_a(B\text{-}C\text{-}D\text{-}A)_n(Y_2)_b$ $(X_3)_a(C\text{-}D\text{-}A\text{-}B)_n(Y_3)_b$ $(X_4)_a(D\text{-}A\text{-}B\text{-}C)_n(Y_4)_b$ wherein
- $X_1$ is D; C-D- or B-C-D-,
- $Y_1$ is -A or -A-B or -A-B-C
- $X_2$ is A-, D-A- or C-D-A-
- $Y_2$ is -B, -B-C or B-C-D
- $X_3$ is B-, A-B-, D-A-B-
- $Y_3$ is -C, -C-D, -C-D-A
- $X_4$ is C-, B-C-, A-B-C-.
- $Y_4$ is -D, -D-A, -D-A-B
- a is 0 or 1; b is 0 or 1
- and n is at least 4.

It is to be understood that the peptide chain may include amino acids between the hereinabove noted groups of four amino acids provided that the spacing between such groups and the charge on the amino acids does not change the characteristics of the peptide chain which provide amphiphilicity and a positive charge and do not adversely affect the folding characteristics of the chain to that which is significantly different from one in which the hereinabove noted group of four amino acids are not spaced from each other.

As representative examples of peptides in accordance with the present invention, there may be mentioned.

I  Ala-Phe-Ser-Lys-Ala-Phe-Ser-Lys-Ala-Phe-Ser-Lys-Ala-Phe-Ser-Lys-Ala-Phe-Ser-Lys

II  Ala-Phe-Ser-Lys-Ala-Phe-Ser-Lys-Ala-Phe-Ser-Lys-Ala-Phe-Ser-Lys-Ala-Phe-Ser-Lys.

III  Phe-Ser-Lys-Ala-Phe-Ser-Lys-Ala-Phe-Ser-Lys-Ala-Phe-Ser-Lys-Ala-

IV  Ser-Lys-Ala-Phe-Ser-Lys-Ala-Phe-Ser-Lys-Ala-Phe-Ser-Lys-Ala-Phe-Ser-Lys-Ala-Phe

V  Lys-Ala-Phe-Ser-Lys-Ala-Phe-Ser-Lys-Ala-Phe-Ser-Lys-Ala-Phe-Ser

The peptide may have amino acids extending from either end of the chain. For example, the chains may have a Ser-Lys sequence before the "Ala" end, and/or an Ala-Phe sequence after the "Lys" end. Other amino acid sequences may also be attached to the "Ala" and-/or the "Lys" end.

Similarly, in any polypeptide chain having at least four groups of amino acids of the sequence as described above, the chain may have, for example, a C-D sequence before the first A-B-C-D group. Also other amino acid sequences may be attached to the "A" and-/or the "D" end of one of these polypeptide chains. Also there may be amino acids in the chain which space one or more groups of the hereinabove noted four amino acids from each other.

The peptides may be produced by known techniques and obtained in substantially pure form. For example, the peptides may be synthesized on an automatic synthesizer. *Journal of the American Chemical Society*, Vol. 85 Pages 2149-54(1963). It is also possible to produce such peptides by genetic engineering techniques.

In accordance with another preferred embodiment, the peptide employed may be a magainin peptide.

A magainin peptide is either a magainin such as Magainin I, II or III or an analogue or derivative thereof. The magainin peptides may include the following basic peptide structure $X_{12}$:

$-R_{11}\text{-}R_{11}\text{-}R_{12}\text{-}R_{13}\text{-}R_{11}\text{-}R_{14}\text{-}R_{12}\text{-}R_{11}\text{-}R_{14}\text{-}$ $R_{12}\text{-}R_{11}\text{-}R_{11}\text{-}R_{11}\text{-}R_{14a}\text{-}(R_{15})_n\text{-}R_{14a}\text{-}R_{14}\text{-}$ wherein $R_{11}$ is a hydrophobic amino acid, $R_{12}$ is a basic hydrophilic amino acid; $R_{13}$ is a hydrophobic, neutral hydrophilic, or basic hydrophilic amino acid; $R_{14}$ and $R_{14a}$ are hydrophobic or basic hydrophilic amino acids, $R_{15}$ is glutamic acid or aspartic acid, or a hydrophobic or basic hydrophilic amino acid, and n is 0 or 1. In a preferred embodiment, $R_{13}$ is a hydrophobic or neutral hydrophilic amino acid, $R_{14a}$ is a hydrophobic amino acid, and $R_{15}$ is glutamic acid or aspartic acid.

Thus, for example, a magainin peptide may include the following structure:

$Y_{12}\text{-}X_{12}$, where $X_{12}$ is the hereinabove described basic peptide structure and $Y_{12}$ is
- (i) $R_{12}$
- (ii) $R_{14a}\text{-}R_{12}$;
- (iii) $R_{11}\text{-}R_{14a}\text{-}R_{12}$; or
- (iv) $R_{14}\text{-}R_{11}\text{-}R_{14a}\text{-}R_{12}$ where $R_{11}$, $R_{12}$, $R_{14}$, and $R_{14a}$ are as previously defined.

A magainin peptide may also have the following structure:

$-X_{12}\text{-}Z_{12}\text{-}$ wherein $X_{12}$ is as previously defined and $Z_{12}$ is:
(i) $R_{16}$ where $R_{16}$ is a basic hydrophilic amino acid or asparagine or glutamine; or
(ii) $R_{16}$-$R_{17}$ where $R_{17}$ is a neutral hydrophilic amino acid, a hydrophobic amino acid, or a basic hydrophilic amino acid. Preferably, $R_{17}$ is a neutral hydrophilic amino acid.

A magainin peptide may also have the following structure:

$(Y_{12})_a$-$X_{12}$-$(Z_{12})_b$ where $X_{12}$, $Y_{12}$, and $Z_{12}$ are as previously defined, and a is 0 or 1 and b is 0 or 1.

The magainin peptides may also include the following basic peptide structure $X_{13}$:

$R_{14}$-$R_{11}$-$R_{14a}$-$R_{12}$-$R_{11}$-$R_{11}$-$R_{12}$-$R_{13}$-$R_{11}$-$R_{14}$-

$R_{12}$-$R_{11}$-$R_{11}$-$R_{12}$-, wherein $R_{11}$, $R_{12}$, $R_{13}$, $R_{14}$, and $R_{14a}$ are amino acids as hereinabove described.

The magainin peptide may also include the following structure $X_{13}$-$Z_{13}$; wherein $X_{13}$ is the hereinabove described basic peptide structure and $Z_{13}$ is $(R_{11})_n$-$(R_{11})_n$-$(R_{11})_n$-$(R_{14a})_n$-$(R_{15})_n$-$(R_{14a})_n$-

$(R_{14})_n$-$(R_{16})_n$-$(R_{17})_n$-, wherein $R_{11}$, $R_{14}$, $R_{14a}$, $R_{15}$, $R_{16}$, and $R_{17}$ are amino acids as hereinabove described, and n is 0 or 1, and each n may be the same or different.

The magainin peptides generally include at least fourteen amino acids and may include up to forty amino acids. A magainin peptide preferably has 22 or 23 amino acids. Accordingly, the hereinabove described basic peptide structures of a magainin peptide may include additional amino acids at the amino end or at the carboxyl end, or at both ends.

As representative examples of such magainin peptides, there may be mentioned peptides having the following primary sequence (expressed as a single letter code) as well as appropriate analogues and derivatives thereof:
(a) (NH$_2$) GIGKFLHSAGKFGKAFVGEIMKS(OH) or (NH$_2$) (Magainin I)
(b) (NH$_2$) GIGKFLHSAKKFGKAFVGEIMNS(OH) or (NH$_2$) (Magainin II)
(c) (NH$_2$) GIGKFLHSAKKFGKAFVGEIMN(OH) or (NH$_2$) (Magainin III)

The following are examples of peptide derivatives or analogs of the basic structure:
(d) (NH$_2$) IGKFLHSAKKFGKAFVGEIMNS(OH) or (NH$_2$)
(e) (NH$_2$) GKFLHSAKKFGKAFVGEIMNS(OH) or (NH$_2$)
(f) (NH$_2$) KFLHSAKKFGKAFVGEIMNS(OH) or (NH$_2$)

Magainin peptides are described in *Proc. Natl. Acad Sci.* Vol. 84 pp. 5449-53 (Aug. 1987). The term "magainin peptides" as used herein refers to the basic magainin structure as well as derivatives and analogs thereof, including but not limited to the representatives derivatives or analogs.

In accordance with a further embodiment, the peptide employed may be a PGLa peptide or an XPF peptide.

A PGLa peptide is either PGLa or an analogue or derivative thereof. The PGLa peptides preferably include the following basic peptide structure $X_{14}$:

—$R_{11}$—$R_{17}$—$R_{12}$—$R_{11}$—$R_{14}$—$R_{14}$—$R_{11}$—

$R_{11}$—$R_{14}$—$R_{12}$—$R_{11}$—$R_{11}$—$R_{12}$—$R_{11}$—

$R_{11}$—$R_{11}$—$R_{12}$— where $R_{11}$, $R_{12}$, $R_{14}$, and $R_{17}$ are as previously defined.

The PGLa peptides generally include at least seventeen amino acids and may include as many as forty amino acids. Accordingly, the hereinabove described basic peptide structure for a PGLa peptide may include additional amino acids at the amino end or at the carboxyl end or at both the amino and carboxyl end.

Thus, for example, a PGLa peptide may have the following structure:

-$Y_{14}$-$X_{14}$- where $X_{14}$ is as previously defined and $Y_{14}$ is
(i) $R_{11}$;
(ii) $R_{14}$-$R_{11}$
where $R_{11}$ is as previously defined.

For example, a PGLa like peptide may also have the following structure:

-$X_{14}$-$Z_{14}$- where $X_{14}$ is as previously defined; and $Z_{14}$ is:
(i) $R_{11}$; or
(ii) $R_{11}$-$R_{11}$
where $R_{11}$ is as previously defined.

A PGLa peptide may also have the following structure:

$(Y_{14})_a$-$X_{14}$-$(Z_{14})_b$ where $X_{14}$; $Y_{14}$ and $Z_{14}$ are as previously defined, a is 0 or 1 and b is 0 or 1.

An XPF peptide is either XPF or an analogue or derivative thereof. The XPF peptides preferably include the following basic peptide structure $X_{16}$:

—$R_{11}$—$R_{17}$—$R_{12}$—$R_{11}$—$R_{14}$—$R_{18}$—$R_{17}$—

$R_{11}$—$R_{14}$—$R_{12}$—$R_{11}$—$R_{11}$—$R_{12}$—

$R_{11}$—$R_{11}$—$R_{11}$—$R_{12}$—$(R_{15})_n$—$R_{11}$—.

wherein $R_{11}$, $R_{12}$, $R_{14}$, $R_{15}$ and $R_{17}$ are as previously defined and $R_{18}$ is glutamine or asparagine, or a basic hydrophilic, or hydrophobic amino acid, and n is 0 or 1.

The XPF peptides generally include at least nineteen amino acids and may include up to forty amino acids. Accordingly, the hereinabove described basic peptide structure of XPF may include additional amino acids at the amino end, or at the carboxyl end or at both the amino and carboxyl ends.

Thus, for example, an XPF peptide may include the following structure:

-$Y_{16}$-$X_{16}$- where $X_{16}$ is as previously defined and $Y_{16}$ is
(i) $R_{11}$ or
(ii) $R_{14}$-$R_{11}$ where $R_{11}$ and $R_{14}$ are is as previously defined.

An XPF peptide may include the following structure:

$$-X_{16}-Z_{16}-$$

where $X_{16}$ is as previously defined and $Z_{16}$ is
(i) $R_{11}$; or
(ii) $R_{11}$-$R_{18}$; or
(iii) $R_{11}$-$R_{18}$-Proline; or
(iv) $R_{11}$-$R_{18}$-Proline-$R_{12}$ An XPF peptide may also have the following structure:

$$(Y_{16})_a\text{-}X_{16}\,(Z_{16})_b$$

where $X_{16}$, $Y_{16}$ and $Z_{16}$ are as previously defined: a is 0 or 1 and b is 0 or 1.

Preferred are XPF or PGLa peptides, which are characterized by the following primary amino acid sequence (single letter amino acid code):

PGLa: GMASKAGAIAGKIAKVALKAL (NH$_2$)
XPF: GWASKIGQTLGKIAKVGLKELIQPK

A review of XPF and PGLa can be found in Hoffman et al, *EMBO J.* 2:711–714, 1983; Andreu et al, *J. Biochem.* 149:531–535, 1985; Gibson et al *J. Biol. Chem.* 261:5341–5349, 1986; and Giovannini et al, *Biochem J.* 243:113–120, 1987.

In accordance with yet another embodiment, the peptide employed may be a CPF peptide or appropriate analogue or derviative thereof.

A basic CPF peptide structure as well as analogues and derivatives thereof are herein sometimes referred to collectively as CPF peptides.

The CPF peptide is preferably one which includes the following peptide structure $X_{30}$:

$$-R_{21}-R_{21}-R_{22}-R_{22}-R_{21}R_{21}-R_{23}-R_{21}-$$

$$-R_{21}-R_{21}-R_{23}-R_{21}-R_{21}-R_{24}-R_{25}-R_{21}-$$

wherein $R_{21}$ is a hydrophobic amino acid;

$R_{22}$ is a hydrophobic amino acid or a basic hydrophilic amino acid;

$R_{23}$ is a basic hydrophilic amino acid; and $R_{24}$ is a hydrophobic or neutral hydrophilic amino acid; and $R_{25}$ is a basic or neutral hydrophilic amino acid.

The hereinabove basic structure is hereinafter symbolically indicated as $X_{30}$.

The hydrophobic amino acids may be Ala, Cys, Phe, Gly, Ile, Leu, Met, Val, Trp, and Tyr.

The neutral hydrophilic amino acids may be Asn, Gln, Ser, and Thr.

The basic hydrophilic amino acids may be Lys, Arg, His, and ornithine.

The CPF peptide may include only the hereinabove noted amino acids or may include additional amino acids at the amino end or carboxyl end or both the amino and carboxyl end. In general, the peptide does not include more than 40 amino acids.

The CPF peptides including the above basic peptide structure may have from 1 to 4 additional amino acids at the amino end. Accordingly, such preferred peptides may be represented by the structural formula:

$$Y_{30}\text{-}X_{30}\text{-}$$

wherein $X_{30}$ is the hereinabove described basic peptide structure and $Y_{30}$ is
(i) $R_{25}$-, or
(ii) $R_{22}$-$R_{25}$; or
(iii) $R_{21}$-$R_{22}$-$R_{25}$; or
(iv) $R_{22}$-$R_{21}$-$R_{22}$-$R_{25}$; preferably Glycine -$R_{21}$-$R_{22}$-$R_{25}$- wherein $R_{21}$, $R_{22}$, and $R_{25}$ are as previously defined.

The carboxyl end of the basic peptide structure may also have additional amino acids which may range from 1 to 13 additional amino acids.

In a preferred embodiment, the basic structure may have from 1 to 7 additional amino acids at the carboxyl end, which may be represented as follows:

$$-X_{30}\text{-}Z_{30}$$

wherein
$X_{30}$ is the hereinabove defined basic peptide structure and $Z_{30}$ is
(i) $R_{21}$-,
(ii) $R_{21}$-$R_{21}$-;
(iii) $R_{21}$-$R_{21}$-$R_{24}$;
(iv) $R_{21}$-$R_{21}$-$R_{24}$-$R_{24}$;
(v) $R_{21}$-$R_{21}$-$R_{24}$-$R_{24}$-$R_{26}$;
(vi) $R_{21}$-$R_{21}$-$R_{24}$-$R_{24}$-$R_{26}$-Gln; or
(vii) $R_{21}$-$R_{21}$-$R_{24}$-$R_{24}$-$R_{26}$-Gln-Gln, wherein $R_{21}$ and $R_{24}$ are as previously defined, and $R_{26}$ is proline or a hydrophobic amino acid.

Preferred peptides may be represented by the following structural formula:

$$(Y_{30})_a\text{-}X_{30}\text{-}(Z_{30})_b$$

wherein $X_{30}$, $Y_{30}$ and $Z_{30}$ are as previously defined and a is 0 or 1 and b is 0 or 1.

Representative examples of CPF peptides which are useful in the present invention have been described in the literature and comprise the following sequences (single letter amino acid code):

(1) GFGSFLGLALKAALKIGANALGGAPQQ
(2) GLASFLGKALKAGLKIGAHLLGGAPQQ
(3) GLASLLGKALKAGLKIGTHFLGGAPQQ
(4) GLASLLGKALKATLKIGTHFLGGAPQQ
(5) GFASFLGKALKAALKIGANMLGGTPQQ
(6) GFGSFLGKALKAALKIGANALGGAPQQ
(7) GFGSFLGKALKAALKIGANALGGSPQQ
(8) GFASFLGKALKAALKIGANLLGGTPQQ

A review of the CPF peptides can be found in Richter, K., Egger, R., and Kreil (1986) *J. Biol. Chem.* 261, 3676–3680; Wakabayashi, T. Kato, H., and Tachibaba, S. (1985) *Nucleic Acids Research* 13, 1817–1828; Gibson, B. W., Poulter, L., Williams, D. H., and Maggio, J. E. (1986) *J. Biol. Chem.* 261, 5341–5349.

CPF peptides which may be employed in the present invention are represented by the following (single letter amino acid code):

G12S3LG4ALKA5LKIG678LGG9(10)QQ

Where:
1 = F, L
2 = G, A
3 = F, L
4 = K, L
5 = A, G, T

6=A, T
7=H, N
8=A, M, F, L
9=A, S, T
10=P, L

The numbered amino acids may be employed as described in any combination to provide either a basic CPF peptide structure or an analogue or derivative. The term CPF peptide includes the basic peptide structure as well as analogues or derivatives thereof.

In still another embodiment, the peptide employed is a cecropin. The cecropins and analogues and derivatives thereof are described in *Ann. Rev. Microbiol* 1987, Vol. 41 pages 103-26, in particular p. 108 and Christensen at al PNAS Vol. 85 p. 5072-76, which are hereby incorporated by reference.

The term cecropin includes the basic structure as well as analogues and derivatives.

In yet another embodiment, the peptide employed is a sarcotoxin. The sarcotoxins and analogues and derivatives thereof are described in *Molecular Entomology*, pages 369-78, in particular p. 375 Alan R. Liss Inc. (1987), which is hereby incorporated by reference.

The term sarcotoxin includes the basic materials as well as analogues and derivatives.

In another embodiment, an ion channel-forming protein may be used to stimulate or promote wound healing. Ion channel-forming proteins which may be employed include defensins, also known as human neutrophil antimicrobial peptides (HNP), major basic protein (MBP) of eosinophils, bactericidal permeability-increasing protein (BPI), and a pore-forming cytotoxin called variously perforin, cytolysin, or pore-forming protein. Defensins are described in Selsted, et al., *J. Clin. Invest.*, Vol. 76, pgs. 1436-1439 (1985). MBP proteins are described in Wasmoen, et al., *J. Biol. Chem.*, Vol. 263, pgs 12559-12563. (1988). BPI proteins are described in Ooi, et al, *J. Biol. Chem.*, Vol. 262, pgs. 14891-14894 (1987). Perforin is described in Henkart, et al., *J. Exp. Med.*, 160:75 (1984), and in Podack, et al., *J. Exp. Med.*, 160:695 (1984). The above articles are hereby incoroporated by reference.

The term ion channel-forming proteins includes the basic structures of the ion-forming proteins as well as analogues and derivatives.

It is also to be understood that within the scope of the present invention, each of the above-mentioned peptides and proteins may be administered alone, or in combination with one or more of the other above-mentioned peptides and proteins.

The present invention will now be described with respect to the following example; however, the scope of the invention is not to be limited thereby.

EXAMPLE

Twenty-two male rats weighing between 300 g and 325 g were anesthetized, after which their backs and abdomens were shaved and washed with 70% ethanol. Three modified polyvinylchloride sponge discs 2 mm thick and 15 mm in diameter were implanted in each rat abdominally in subcutaneous pockets made under the skin. Two of the implants were cut in half and rejoined before the implantation, and the remaining disc was sandwiched between two silicone discs which forced granulation tissue infiltration to occur from the periphery of the disc. A single 15 mm×15 mm square full excision wound was made on the back and the wound edges tattooed.

The rats were then divided into four groups. A first, or control, group of four rats received sham injections daily. A second group of four rats received daily intramuscular injections of 10 mg of cortisone acetate. Cortisone is known to be an inhibitor of wound healing. A third group of seven rats received daily intramuscular injections of 0.3 mg of amide-terminated Magainin II. A fourth group of seven rats received daily intramuscular injections of 10 mg of cortisone acetate and 0.3 mg of Magainin II at separate sites. At seven days, rat weights were recorded, wound sizes measured, and the implants harvested. The staple which joined the two disc halves together was carefully removed and the breaking strength measured. Collagen content from the implant halves from each treatment group was measured by weighing the pepsin extracted native collagen. The sponge halves are homogenized in 0.5M ice-cold acetic acid containing 0.1 mg of pepsin per ml. The homogenate was stirred for 24 hours at 4° C., centrifuged, and supernatants saved. The native solubilized collagen was isolated by adding sodium chloride to 10% w/v. The salt precipitate was collected by centrifugation (10,000× g for 10 min.) and then taken up in 145 mM potassium phosphate buffer pH7.6, exhaustively dialyzed against 1 mM HCl, lyophilized and its dry weight recorded. Confirmation of collagen purity was made by SDS polyacrylamide gel electrophoresis. Pepsin digestion extracts only native collagen, needed for the formation of collagen fibers. The accumulations of collagen in the early stages of healing are responsible for gain in wound tensile strength. Collagen content from the implants taken from the group treated with cortisone acetate alone averged 0.82 mg/sponge, as compared with 3.43 mg/sponge for the control group. The group treated with cortisone acetate and Magainin II had an average collagen content of 3.20 mg/sponge. The group treated with Magainin II alone had an average collagen content of 3.82 mg/sponge.

The group treated with cortisone acetate alone had an average wound breaking strength of 195 g, as compared to 440 g for the control group. The group treated with cortisone acetate and Magainin II had an average wound breaking strength of 320 g. The group treated with Magainin II alone has a average wound breaking strength of 415 g.

The control group had an average wound contraction of 67%, while the group treated with cortisone acetate alone had an average wound contraction of 28%. The group treated with cortisone acetate and Magainin II had an average wound contraction of 53%, and the group treated with Magainin II alone had an average wound contraction of 65%.

The above results indicate that Magainin II is antagonistic of cortisone inhibition of wound healing in that Magainin II helped restore new connective tissue (e.g., collagen) deposition as well as wound contraction. Antagonism of inhibited wound contraction is a significant finding in that other antagonists such as Vitamin A, anabolic steroids, and growth hormone were effective in restoring connective tissue deposition, but were ineffective in restoring wound contraction. Thus, it is shown that a Magainin II peptide, in addition to its known antimicrobial, or antibiotic, properties, is also effective in stimulating wound healing.

The biologically active peptide may be employed for wound treatment and healing for a wide variety of hosts. The host may be a human or non-human animal.

The biologically active peptide may be employed in a wide variety of pharmaceutical compositions in combination with a non-toxic pharmaceutical carrier or vehicle such as a filler, non-toxic buffer, or physiological saline solution. Such pharmaceutical compositions, when used systemically, may be in the form of a liquid, for example, as an injectable solution. The peptide may also be used in combination with adjuvants, protease inhibitors, or compatible drugs where such a combination is seen to be desirable or advantageous (e.g., in controlling infection caused by harmful microorganisms).

The peptide is administered to the host in an amount effective to stimulate healing of a wound in a host.

Numerous modifications and variations of the present invention are possible in light of the above teachings and, therefore, within the scope of the accompanying claims, the invention may be practiced otherwise than as particularly described.

What is claimed is:

1. A process for treating a wound in a host, comprising administering to a host having a wound at least one biologically active amphiphilic peptide and/or biologically active protein, said peptide or protein being an ion channel-forming peptide or protein, said at least one biologically active amphiphilic peptide or protein being administered in an amount effective for treating a wound in the host.

2. The process of claim 1 wherein the peptide is a basic polypeptide having at least sixteen amino acids, wherein said basic polypeptide includes at least eight hydrophobic amino acids and at least eight hydrophilic amino acids.

3. The process of claim 2 wherein said polypeptide comprises a chain of at least four groups of amino acids, each of said at least four groups consisting of four amino acids, wherein two of the four amino acids in each group are hydrophobic amino acids, and two of the four amino acids in each group are hydrophilic amino acids, with at least one of the hydrophilic amino acids in each group being a basic hydrophilic amino acid and the other hydrophilic amino acid being a basic or neutral hydrophilic amino acid.

4. The process of claim 3 wherein each of said groups of four amino acids is of the sequence ABCD, BCDA, CDAB, or DABC, wherein A and B are each hydrophobic amino acids and may be the same or different, one of C or D is a basic hydrophilic amino acid, and the other of C or D is a basic or neutral hydrophilic amino acid and may be the same or different.

5. The process of claim 1 wherein the peptide is a magainin peptide.

6. The process of claim 5 wherein said magainin peptide includes the following basic peptide structure:

$$-R_{11}-R_{11}-R_{12}-R_{13}-R_{11}-R_{14}-R_{12}-R_{11}-R_{14}-$$

$$-R_{12}-R_{11}-R_{11}-R_{11}-R_{14a}-(R_{15})_n-R_{14a}-R_{14}--$$

wherein $R_{11}$ is a hydrophobic amino acid, $R_{12}$ is a basic hydrophilic amino acid, $R_{13}$ is a hydrophobic, neutral hydrophilic, or basic hydrophilic amino acid, $R_{14}$ and $R_{14}$ are hydrophobic or basic hydrophilic amino acids, $R_{15}$ is glutamic acid or aspartic acid, a hydrophobic amino acid, or a basic hydrophilic amino acid, and n is 0 or 1.

7. The process of claim 6 wherein $R_{13}$ is a hydrophobic or neutral hydrophilic amino acid.

8. The process of claim 6 wherein $R_{14a}$ is a hydrophobic amino acid.

9. The process of claim 6 wherein $R_{15}$ is glutamic acid or aspartic acid.

10. The process of claim 5 wherein said magainin peptide is of the following basic peptide structure:

$$--R_{14}-R_{11}-R_{14a}-R_{12}-R_{11}-R_{11}-R_{12}-R_{13}-R_{11}-$$

$$R_{14}-R_{12}-R_{11}-R_{11}-R_{12}--,$$

wherein $R_{11}$ is a hydrophobic amino acid, $R_{12}$ is a basic hydrophilic amino acid, $R_{13}$ is a hydrophobic, neutral hydrophilic, or basic hydrophilic amino acid, and $R_{14}$ and $R_{14a}$ are hydrophobic or basic hydrophilic amino acids.

11. The process of claim 10 wherein $R_{13}$ is a hydrophobic or neutral hydrophilic amino acid.

12. The process of claim 10 wherein $R_{14a}$ is a hydrophobic amino acid.

13. The process of claim 1 wherein the peptide is a cecropin.

14. The process of claim 1 wherein the peptide is a sarcotoxin.

15. The process of claim 1 wherein the peptide is a XPF peptide.

16. The process of claim 1 wherein the peptide is a PGLa peptide.

17. The process of claim 1 wherein the peptide is a CPF peptide.

18. The process of claim 1 wherein the peptide is administered systemically.

19. A process for treating a wound in a host, comprising adminstering to a host having a wound at least one biologically active amphiphilic peptide selected from the class consisting of magainin peptides, cecropins, sarcotoxins, PGLa peptides, CPF peptides, and XPF peptides, said at least one biologically active amphiphilic peptide being administered in an amount effective for treating a wound in the host.

20. The process of claim 19 wherein the peptide is magainin peptide.

21. The process of claim 19 wherein the peptide is a cecropin.

22. The process of claim 19 wherein the peptide is a sarcotoxin.

23. The process of claim 19 wherein the peptide is a CPF peptide.

24. The process of claim 19 wherein the peptide is is an XPF peptide.

25. The process of claim 5 wherein said magainin peptide is:

(NH$_2$)GIGKFLHSAKKFGKAFV-GEIMNS(NH$_2$).

26. The process of claim 20 wherein said magainin peptide includes the following basic peptide structure:

$$--R_{11}-R_{11}-R_{12}-R_{13}-R_{11}-R_{14}-R_{12}-R_{11}-R_{14}-$$

$$R_{12}-R_{11}-R_{11}-R_{11}-R_{14a}-(R_{15})_n-R_{14a}-R_{14}--,$$

wherein $R_{11}$ is a hydrophobic amino acid, $R_{12}$ is a basic hydrophilic amino acid, $R_{13}$ is a hydrophobic, neutral hydrophilic, or basic hydrophilic amino acids, $R_{14}$ and $R_{14a}$ are hydrophobic or basic hydrophilic amino acids, $R_{15}$ is a glutamic acid or aspartic acid, a hydrophobic amino acid, or a basic hydrophilic amino acid, and n is 0 or 1.

27. The process of claim 26, wherein $R_{13}$ is a hydrophobic or neutral hydrophilic amino acid.

28. The process of claim 26 wherein $R_{14a}$ is a hydrophobic amino acid.

29. The process of claim 26 wherein $R_{15}$ is a glutamic acid or aspartic acid.

30. The process of claim 20 wherein said magainin peptide is of the following basic peptide structure.

--$R_{14}$-$R_{11}$-$R_{14a}$-$R_{12}$-$R_{11}$-$R_{11}$-$R_{12}$-$R_{13}$-$R_{11}$-

$R_{14}$-$R_{12}$-$R_{11}$-$R_{11}$-$R_{12}$, wherein $R_{11}$ is a hydrophobic amino acid, $R_{12}$ is a basic hydrophilic amino acid, $R_{13}$ is a hydrophobic, neutral hydrophilic, or basic hydrophilic amino acid, and $R_{14}$ and $R_{14a}$, are hydrophobic or basic hydrophilic amino acids.

31. The process of claim 30 wherein $R_{13}$ is a hydrophobic or neutral hydrophilic amino acid.

32. The process of claim 30 wherein $R_{14a}$ is a hydrophobic amino acid.

33. The process of claim 20 wherein said magainin peptide is:

(NH$_2$)GIGKFLHSAKKFGKAFV-GEIMNS(NH$_2$).

* * * * *